(12) United States Patent
Pryor

(10) Patent No.: US 8,206,428 B2
(45) Date of Patent: Jun. 26, 2012

(54) TABBED STENT WITH MINIMUM COMPRESSED PROFILE

(75) Inventor: Jack Pryor, San Diego, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 1069 days.

(21) Appl. No.: 11/219,328

(22) Filed: Sep. 2, 2005

(65) Prior Publication Data

US 2007/0055348 A1   Mar. 8, 2007

(51) Int. Cl.
*A61F 2/06* (2006.01)

(52) U.S. Cl. .......... 623/1.11; 623/1.15; 29/235; 29/282; 29/446

(58) Field of Classification Search .......... 623/1.1, 623/1.15, 1.16, 1.17, 1.18, 1.19, 1.2, 1.22, 623/1.11–1.12; 29/283.5, 515–516, 280, 29/282, 234–235, 446; 72/402; 606/108, 606/198; 128/898
See application file for complete search history.

(56) References Cited

U.S. PATENT DOCUMENTS

| | | | | |
|---|---|---|---|---|
| 5,893,867 A * | 4/1999 | Bagaoisan et al. | ............ | 606/198 |
| 5,925,061 A * | 7/1999 | Ogi et al. | ............ | 623/1.2 |
| 6,159,237 A * | 12/2000 | Alt et al. | ............ | 623/1.11 |
| 6,162,245 A * | 12/2000 | Jayaraman | ............ | 623/1.15 |
| 6,340,366 B2 * | 1/2002 | Wijay | ............ | 623/1.13 |
| 6,579,310 B1 * | 6/2003 | Cox et al. | ............ | 623/1.16 |
| 6,652,579 B1 * | 11/2003 | Cox et al. | ............ | 623/1.34 |
| 6,769,161 B2 * | 8/2004 | Brown et al. | ............ | 29/234 |
| 7,060,089 B2 * | 6/2006 | Ley et al. | ............ | 623/1.15 |
| 7,096,554 B2 * | 8/2006 | Austin et al. | ............ | 29/282 |
| 7,356,903 B2 * | 4/2008 | Krivoruchko et al. | ............ | 29/446 |
| 2002/0123792 A1 * | 9/2002 | Burgermeister | ............ | 623/1.15 |
| 2003/0135970 A1 * | 7/2003 | Thornton | ............ | 29/270 |
| 2007/0005123 A1 * | 1/2007 | Sano et al. | ............ | 623/1.15 |
| 2007/0208413 A1 * | 9/2007 | Nakano | ............ | 623/1.15 |

FOREIGN PATENT DOCUMENTS

| | | | |
|---|---|---|---|
| EP | 1 199 051 | * | 4/2002 |
| EP | 1452151 | | 9/2004 |
| EP | 1452151 A2 | * | 9/2004 |
| WO | WO98/26732 | | 6/1998 |
| WO | WO99/15108 | | 4/1999 |
| WO | WO 2005032424 A1 | * | 4/2005 |
| WO | WO2006/011523 | | 2/2006 |

* cited by examiner

*Primary Examiner* — Corrine M McDermott
*Assistant Examiner* — Mark Mashack

(57) ABSTRACT

A structure and method associated with a tabbed stent that facilitates folding of its unconnected crowns over the adjacent connected crowns, to thus minimize the stent's compressed diameter. The middles of tabs and connected crowns are moved radially inwards with respect to unconnected neighbor crowns such that when in a compressed configuration the unconnected neighbor crowns overlap the connected crowns. The tabs of tabbed stent facilitate folding of the unconnected neighbor crowns over the connected crowns connected to the tabs. In this manner, the compressed profile of the tabbed stent and the crossing profile of the catheter containing the tabbed stent is minimized.

7 Claims, 3 Drawing Sheets

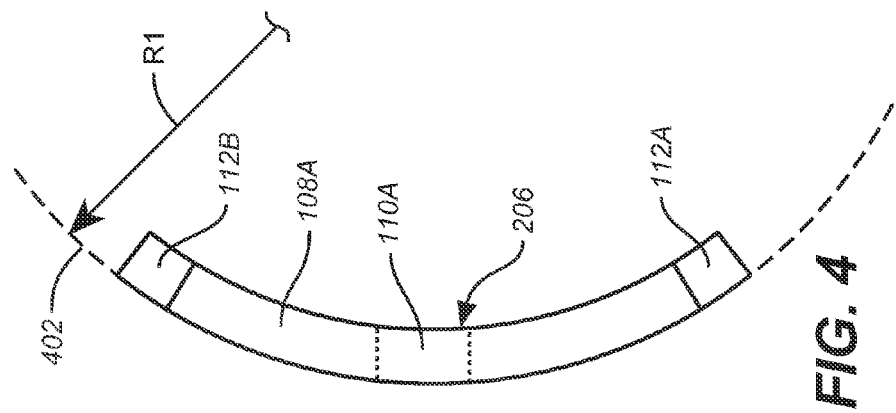
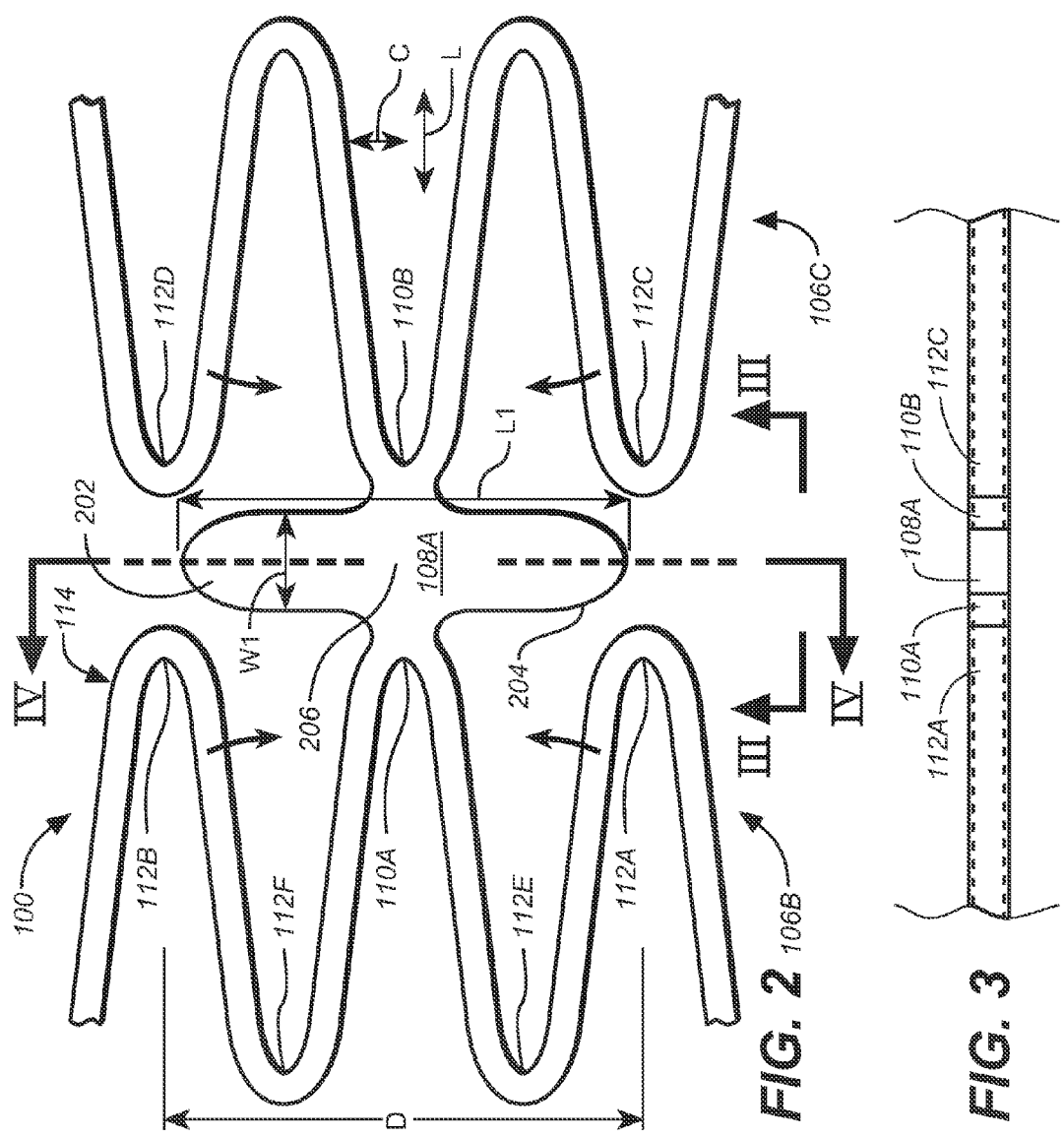

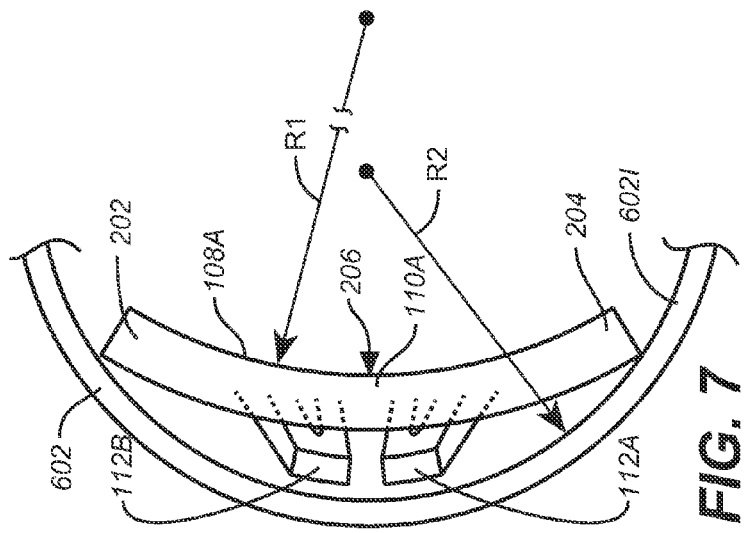
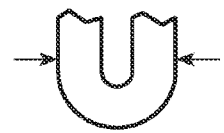
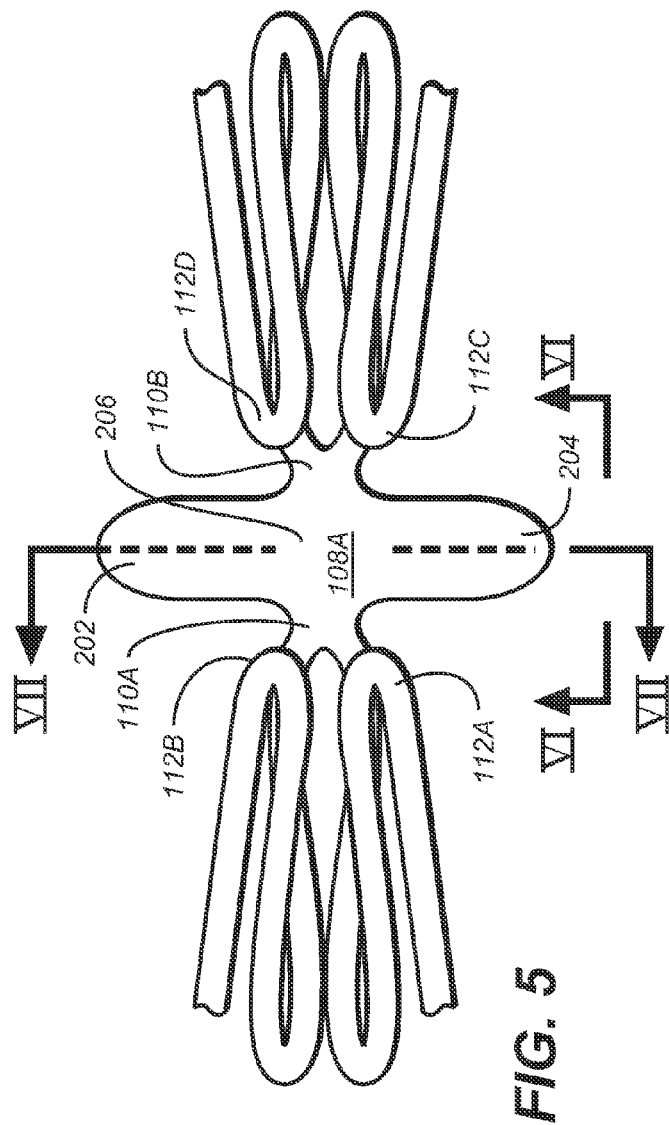
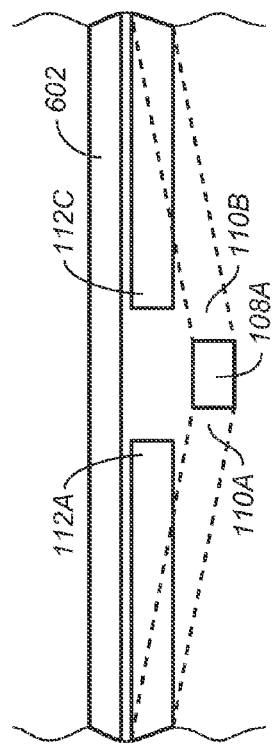
FIG. 5
FIG. 6
FIG. 7
FIG. 8

TABBED STENT WITH MINIMUM COMPRESSED PROFILE

BACKGROUND OF THE INVENTION

1. Field of the Invention

The present invention relates to an intra-luminal device and method. More particularly, the present invention relates to a stent for treatment of intra-luminal diseases in human bodies.

2. Description of the Related Art

In stent deployment systems, a self-expanding stent is restrained within a sheath. After positioning of the stent at the desired location via fluoroscopic guidance, the physician retracts the sheath to deploy the stent, i.e., to expose the stent and allow it to self-expand.

To maximize the range of anatomical variation in which the stent can be used, the stent should have a small compressed profile, i.e., should have a small diameter when restrained within the sheath so that the catheter has a small crossing profile. More particularly, by minimizing the diameter of the stent, the catheter including the stent can also be made very small allowing the catheter to be inserted into very small openings and vessels.

SUMMARY OF THE INVENTION

In accordance with one embodiment, a tabbed stent includes segments having connected crowns and unconnected neighbor crowns folded over the connected crowns. The tabbed stent further includes tabs having first tab ends and second tab ends. The connected crowns are connected to the tabs between the first tab ends and the second tab ends.

A method of loading the tabbed stent into a sheath includes moving the unconnected neighbor crowns closer to the connected crowns and moving middles of the tabs and the connected crowns radially inwards with respect to the unconnected neighbor crowns such that the unconnected neighbor crowns overlap the connected crowns.

The tabs of tabbed stent facilitate folding of the unconnected neighbor crowns over the connected crowns connected to the tabs. In this manner, the compressed profile of the tabbed stent is minimized.

Embodiments in accordance with the present invention are best understood by reference to the following detailed description when read in conjunction with the accompanying drawings.

BRIEF DESCRIPTION OF THE DRAWINGS

FIG. 2 is an enlarged plan view of a section II of the tabbed stent of FIG. 1;

FIG. 3 is a side view of the tabbed stent of FIG. 2 taken from position III;

FIG. 4 is a cross-sectional view of a portion of the tabbed stent of FIG. 2 taken along the line IV-IV of FIG. 2 when the tabbed stent is in its relaxed cylindrical form;

FIG. 5 is an enlarged plan view of the section II of the tabbed stent of FIG. 1 configured to show the inter relationship of stent element as might be observed if that section of the stent was cylindrically compressed;

FIG. 6 is a side view of the tabbed stent of FIG. 5 taken from position VI;

FIG. 7 is a cross-sectional view of a portion of the tabbed stent of FIG. 5 taken along the line VII-VII when the tabbed stent is in its compressed cylindrical form; and FIG. 8 is a plan view showing the width of a crown of the stent.

Common reference numerals are used throughout the drawings and detailed description to indicate like elements.

DETAILED DESCRIPTION

Figure 1:
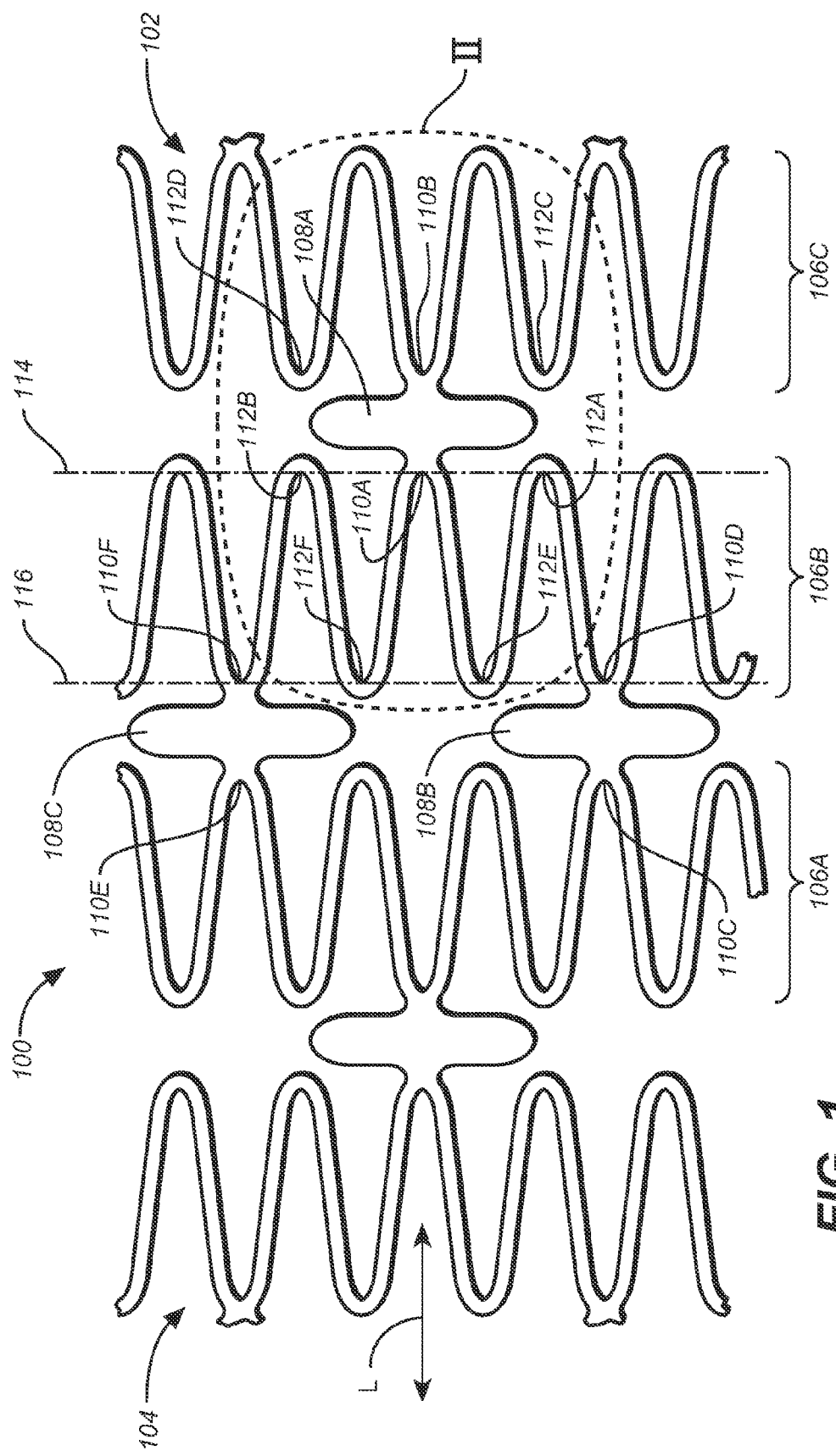
FIG. 1 is a plan view of a section of a laid flat expanded tabbed stent in one embodiment according to the present invention.

Referring to FIG. 1, a tabbed stent 100 includes tabs such as tabs 108A, 108B, 108C. During loading of tabbed stent 100 into a sheath, inward force on the tabs can force the connected crowns radially inwards facilitating the folding of unconnected neighbor crowns over the connected crowns as shown in FIG. 5. In this manner, the compressed profile of tabbed stent 100 is minimized.

More particularly, FIG. 1 is a plan view of a section of a laid flat expanded tabbed stent 100 in one embodiment according to the present invention. Tabbed stent 100 is cylindrical, having a longitudinal axis L. Tabbed stent 100 includes a distal, e.g., first, end 102 and a proximal, e.g., second, end 104.

Illustratively, tabbed stent 100 is integral, i.e., is a single piece and not a plurality of separate pieces connected together. For example, tabbed stent 100 is formed by laser cutting a tubular shaped material. However, tabbed stent 100 can also be formed of separate pieces, which are connected together, e.g., by welding.

Tabbed stent 100 is formed from a plurality of segments such as segments 106A, 106B, 106C. Each segment has a pattern, and this pattern is sometimes called serpentine or an alternating repeating pattern. Segments are coupled to one another at tabs such as tabs 108A, 108B, 108C.

Tabs extend between connected crowns such as connected crowns 110A, 110B, 110C, 110D, 110E, 110F, sometimes called peaks and valleys or minima and maxima, of the alternating repeating patterns of the segments. Specifically, connected crowns of each segment are directly connected to the adjacent connected crowns of the adjacent segment of tabbed stent 100 by the tabs.

To illustrate, segment 106A includes connected crowns 110C, 110E. Segment 106B, sometimes called a first segment, includes connected crowns 110D, 110A, 110F. Segment 106C, sometimes called a second segment, includes connected crown 110B.

Tabs 108A, 108B, 108C, extend between and couple connected crowns 110A, 110B, sometimes called first and second connected crowns, connected crowns 110C, 110D, connected crowns 110E, 110F, respectively. The other connected crowns of the segments are connected to one another by the tabs in a similar manner. In other embodiments every connector between stent segments does not have tabs. For example, in a stent segment with 4 connectors to an adjacent stent segment there would be on 2 connectors with tabs, i.e., not all connectors have tabs.

The tabs include first ends and second ends. The connected crowns are connected to the middle of the tabs between the first ends and a second ends as discussed further below.

Further, the segments further include unconnected crowns that are adjacent to but unconnected to one another. To illustrate, segment 106B includes unconnected crowns 112A, 112B, 112E, 112F. Segment 106C includes unconnected crowns 112C, 112D.

Unconnected crowns 112A and 112C are directly adjacent one another but are unconnected. Similarly, unconnected crowns 112B and 112D are directly adjacent one another but are unconnected.

In accordance with the example illustrated in FIG. 1, in each segment, there are two and only two unconnected crowns between connected crowns. To illustrate, for segment 106B, unconnected crowns 112A and 112E are between connected crowns 110D and 110A. Similarly, unconnected crowns 112F and 112B are between connected crowns 110A and 110F. Although segments of tabbed stent 100 includes two unconnected crowns between connected crowns, in other examples, segments include more or less than two unconnected crowns between connected crowns. For example only 2 tabbed connectors where there are 4 connectors between adjacent stent segments (rings).

In accordance with this example, there are at least two unconnected crowns, sometimes called unconnected neighbor crowns, directly adjacent a connected crown along an edge of a segment, with the connected crown lying between the two unconnected crowns. To illustrate, segment 106B includes a distal edge 114 defined by distal crowns of segment 106 and a proximal edge 116 defined by proximal crowns of segment 106. Connected crown 110A and unconnected crowns 112A, 112B, sometimes called distal crowns, lie along and define distal edge 114.

Further, unconnected crowns 112A, 112B are directly adjacent connected crown 110A along distal edge 114 of segment 106B, with connected crown 110A lying between unconnected crowns 112A, 112B. Accordingly, unconnected crowns 112A, 112B are sometimes called unconnected neighbor crowns of connected crown 110A.

FIG. 2 is an enlarged plan view of a section II of tabbed stent 100 of FIG. 1. FIG. 3 is a side view of tabbed stent 100 of FIG. 2 taken from position III. FIG. 4 is a cross sectional view of tabbed stent 100 of FIG. 2 taken along the line IV-IV of FIG. 2 when tabbed stent 100 is in its relaxed (expanded) cylindrical form. In FIGS. 3 and 4 (and FIGS. 6, 7), a minor difference in thickness is shown to illustrate features of tabbed stent 100. However, this is for purposes of illustration only, and the thickness of tabbed stent 100 is typically uniform such that the elements would be superimposed upon on another in the view of FIG. 3.

Referring now to FIGS. 2, 3 and 4 together, tab 108A has a circumferential length L1 between a first tab end 202 and a second tab end 204, i.e., the length of tab 108A along the circumferential direction C of tabbed stent 100. Further, tab 108A has a longitudinal width W1, i.e., the width of tab 108A along longitudinal axis L between connected crowns 110A, 110B. In this example, circumferential length L1 is greater than longitudinal width W1. There's no critical length L1 to width W1 ratio. What is critical is the width (in the vertical direction as drawn) relative to the radius of curvature and the radius of the sheath. The tab must have a bending radius greater than the sheath and the tab must be wide enough so that the connected crown moves radially inward a distance about equal to the wall thickness of the stent. This assumes that the unconnected crowns sit perfectly flat against the sheath. In reality, their width and radius of curvature will tend to move them radially inward as well. Though it is usually a negligible distance.

Connected crowns 110A, 110B are connected to the middle 206, sometimes called central portion, of tab 108A. More particularly, connected crowns 110A, 110B are connected to tab 108A between first and second tab ends 202, 204.

Further, circumferential length L1 is approximately equal to the distance between adjacent unconnected neighbor crowns, i.e., between unconnected crowns having a connected crown in between along an edge of a segment. To illustrate, circumferential length L1 is approximately equal to the distance D between unconnected crowns 112A and 112B having connected crown 110A in between along distal edge 114 of segment 106B. When the stent is laser-cut from a tube, we assume that tabs and crowns have equal radii of curvature, then the tab will need to be substantially wider than a crown, e.g., likely about 3 times the width, for it to move radially inward by about the wall thickness of the stent. The width of a crown is defined as the inside diameter of the curve forming the peak of the crown (where the stent construction transitions from its straight strut section to the peak curve) plus the width (thickness in a radial direction) of the crown section that connects to the straight strut portion. The distance between arrows as shown in FIG. 8.

As shown in FIGS. 3 and 4, tab 108A lies along the outer cylindrical surface of tabbed stent 100. More generally, in its relaxed state, sometimes called deployed or expanded state, as shown in FIG. 4, stent 100 is cylindrically shaped and defines an outer cylindrical surface 402. Outer cylindrical surface 402 has a radius R1, sometimes called a relaxed (expanded) radius.

Thus, in its relaxed state, the tabs, connected crowns, and unconnected crowns of tabbed stent 100 lie along outer cylindrical surface 402. To illustrate, tab 108A, connected crowns 110A, 110B, unconnected crowns 112A, 112B, 112C, 112D lie along outer cylindrical surface 402.

As set forth above, in one example, tabbed stent 100 is formed by laser cutting a tubular shaped material. Accordingly, tabbed stent 100 is the remaining portions of the tubular shaped material and thus remains in a cylindrical shape after cutting.

In another example, the tabs of a tabbed stent similar to tabbed stent 100 are not curved but planar, i.e., lie in a plane instead of on a cylindrical surface, the ends of the tab being the only portion of the tab to touch the outer cylindrical surface 402 when the stent is positioned within a cylindrical lumen.

In one example, the tabs of tabbed stent 100 provide additional external surface area to tabbed stent 100 compared to a stent without the tabs. In one example, the external surface of tabbed stent 100 is coated with a drug as those of skill in the art will understand in light of this disclosure. The additional surface area provided by the tabs of tabbed stent 100 assists with delivery of the drug.

Referring again to FIG. 2, tabbed stent 100 is radially compressed and loaded into a sheath, such as sheath 602 of FIGS. 6 and 7 as discussed further below. Tabbed stent 100 is radially compressed and loaded into a sheath using any one of a number of techniques, e.g., using a funnel, a crimper, or using another stent loading tool. More particularly, during radial compression of tabbed stent 100, an inward force is applied to the tab ends of the tabs as the tabbed stent 100 is passed through the funnel, crimped by the crimper or otherwise compressed by a stent loading tool. Since the tabs retain a radius of curvature greater than that of the stent's compressed radius, the funnel, crimper, or other stent loading tool only presses against (contacts) the tab ends and the tabs extend between the tab ends spaced apart and inwards from the funnel, crimper, or other stent loading tool. As a result, the inward force on the tab ends causes the middles of the tabs and the connected crowns to move inward further than the tab ends and the unconnected crowns as discussed further below in reference to FIGS. 5 and 6.

During this radial compression, segments of tabbed stent 100 are radially compressed to a reduced diameter. This causes the crowns of the segments to move closer to one another, i.e., the distance between adjacent crowns along edges of the segments is reduced, as with conventional stents.

To illustrate, unconnected crowns 112A, 112B and unconnected crowns 112C, 112D move towards connected crown 110A and connected crown 110B, respectively, as indicated by the arrows. At the same time, ends of the tabs contact the sheath, funnel, crimps, or other stent loading tool, pushing them radially inward. Accordingly, the middles of the tabs and thus connected crowns move radially inwards relative to the unconnected crowns. This facilitates folding of the unconnected crowns over the connected crowns connected to the tabs as discussed below.

FIG. 5 is an enlarged plan view of the section II of tabbed stent 100 of FIG. 1 in its compressed cylindrical form, e.g., when restrained within a sheath (not shown in FIG. 5, see sheath 602 in FIGS. 6 and 7). FIG. 6 is a side view of tabbed stent 100 of FIG. 5 taken from position VI. FIG. 7 is a cross sectional view of tabbed stent 100 of FIG. 5 taken along the line VII-VII when tabbed stent 100 is in its compressed cylindrical form.

Referring now to FIGS. 5 and 6 together, when in its compressed form, unconnected crowns are folded over, sometimes called overlapped on, connected crowns thus resulting in a minimum compressed profile for tabbed stent 100. To illustrate, unconnected crowns 112A, 112B and unconnected crowns 112C, 112D are folded over (overlapped on) connected crown 110A and connected crown 110B, respectively. More particularly, connected crown 110A and connected crown 110B are radially inwards with respect to unconnected crowns 112A, 112B and unconnected crowns 112C, 112D.

The tabs of tabbed stent 100 facilitate the folding of the unconnected crowns over the connected crowns. Referring now to FIG. 7, as tabbed stent 100 is loaded into and/or restrained within sheath 602, the unconnected crowns press against cylindrical inner surface 602I of sheath 602 (or a funnel, crimper or other stent loading tool) and thus lie along the cylindrical inner surface 602I of sheath 602. To illustrate, unconnected crowns 112A, 112B lie along the cylindrical inner surface 602I of sheath 602.

However, as tabbed stent 100 is loaded into sheath 602, the tabs retain a radius of curvature greater than that of the compressed stent (they may experience some distortion albeit small). Accordingly, only the tab ends of the tabs press against (contact) cylindrical inner surface 602I of sheath 602 and the tabs extend between the tab ends spaced apart from the cylindrical inner surface 602I of sheath 602. Stated another way, the radius R1 of the tabs is greater than the radius R2 of cylindrical inner surface 602I of sheath 602 such that only the tab ends of the tabs pressed against sheath 602 and the middles of the tabs are spaced apart from cylindrical inner surface 602I of sheath 602.

To illustrate, tab ends 202, 204 of tab 108A press against cylindrical inner surface 602I of sheath 602. Sheath 602 can also be representative of a funnel, crimper, or other stent loading tool during loading of tabbed stent 100 into a sheath. Tab 108A extends between tab ends 202, 204 and is spaced apart from cylindrical inner surface 602I of sheath 602 between tab ends 202, 204. Since connected crowns 110A, 110B are connected to the middle 206 of tab 108A, connected crowns 110A, 110B are also spaced apart from cylindrical inner surface 602I of sheath 602. Conversely, as set forth above, unconnected crowns 112A, 112B lie along the cylindrical inner surface 602I of sheath 602. Accordingly, the middle 206 of tab 108A and thus connected crowns 110A, 110B are located radially inwards with respect to unconnected crowns 112A, 112B. Thus, unconnected crowns 112A, 112B are readily folded over connected crown 110A as the compressed diameter is reduced further.

When tabbed stent 100 is in its compressed form as illustrated in FIGS. 5, 6, and 7, tabbed stent 100 has a minimum compressed diameter. More particularly, instead of having a plurality of crowns radially adjacent one another, the tabs of tabbed stent 100 facilitate folding of the unconnected crowns over the connected crowns connected to the tabs. In this manner, the compressed profile of tabbed stent 100 is minimized so that the catheter containing tabbed stent 100 has a small crossing profile.

In one example, tabbed stent 100 is formed from a memory metal such as nickel titanium alloy, e.g., nitinol. In accordance with this example, upon retraction of sheath 602, tabbed stent 100, i.e., a self-expanding stent, self-expands to its original expanded form. Further, the tabs of tabbed stent 100 maximize radiopacity (fluoroscopic visibility) of tabbed stent 100 thus facilitating guidance to the treatment site.

This disclosure provides exemplary embodiments according to the present invention. Numerous variations, whether explicitly provided for by the specification or implied by the specification or not, such as variations in structure, dimension, type of material and manufacturing process may be implemented by one of skill in the art in view of this disclosure.

What is claimed is:

1. A method of loading a stent into a sheath, wherein prior to said loading, said stent comprises:
   a first segment comprising:
      a plurality of connected crowns along an edge of said first segment comprising a first connected crown along an edge of said first segment;
      a plurality of unconnected crowns along said edge of said first segment comprising:
      a first unconnected neighbor crown directly adjacent but spaced apart from said first connected crown; and
      a second unconnected neighbor crown directly adjacent but spaced apart from said first connected crown;
         wherein two and only two of said plurality of unconnected crowns along said edge of said first segment are between each connected crown along said edge of said first segment, said connected crowns being connected to tabs;
   a first tab of said tabs comprising:
      a first tab end; and
      a second tab end, wherein said first connected crown is connected to approximately a middle of said first tab between said first tab end and said second tab end, said method comprising:
   moving said first and second unconnected neighbor crowns closer to said first connected crown; and
   moving said middle of said first tab and said first connected crown radially inwards with respect to said first and second unconnected neighbor crowns by applying an inward force to only said first tab end and said second tab end, wherein said first and second unconnected neighbor crowns overlap said first connected crown, wherein said first connected crown is spaced apart from said sheath.

2. A method of loading a stent into a sheath, wherein prior to said loading, said stent comprises:
   a first segment comprising:
      a plurality of connected crowns along an edge of said first segment comprising a first connected crown;
      a plurality of unconnected crowns along said edge of said first segment comprising:
      a first unconnected neighbor crown directly adjacent but spaced apart from said first connected crown; and
      a second unconnected neighbor crown directly adjacent but spaced apart from said first connected crown;

wherein two and only two of said plurality of unconnected crowns along said edge of said first segment are between each connected crown along said edge of said first segment, said connected crowns being connected to tabs;
a first tab of said tabs comprising:
a first tab end; and
a second tab end, wherein said first connected crown is connected to approximately a middle of said first tab between said first tab end and said second tab end, said method comprising:
moving unconnected crowns of stent segments circumferentially closer to connected crowns connected to tabs of said stent comprising moving said first and second unconnected neighbor crowns closer to said first connected crown; and
moving middles of said tabs and said connected crowns radially inwards with respect to said unconnected crowns by applying an inward force to only first tab ends and second tab ends of said tabs, wherein said unconnected crowns overlap said connected crowns including said first and second unconnected neighbor crowns overlapping said first connected crown.

3. A method of loading a stent into a sheath, wherein prior to said loading, said stent comprises:
a first segment comprising:
a plurality of connected crowns along an edge of said first segment comprising a first connected crown along an edge of said first segment;
a plurality of unconnected crowns along said edge of said first segment comprising:
a first unconnected neighbor crown directly adjacent but spaced apart from said first connected crown; and
a second unconnected neighbor crown directly adjacent but spaced apart from said first connected crown;
wherein two and only two of said plurality of unconnected crowns along said edge of said first segment are between each connected crown along said edge of said first segment, said connected crowns being connected to tabs;
a first tab of said tabs comprising:
a first tab end; and
a second tab end, wherein said first connected crown is connected to approximately a middle of said first tab between said first tab end and said second tab end, said method comprising:
moving said first and second unconnected neighbor crowns closer to said first connected crown; and
moving said middle of said first tab and said first connected crown radially inwards with respect to said first and second unconnected neighbor crowns by applying an inward force to only said first tab end and said second tab end, wherein said first and second unconnected neighbor crowns overlap said first connected crown, wherein said tabs have a first radius of curvature before and after said loading.

4. A method of loading a stent into a sheath, wherein prior to said loading, said stent comprises:
a first segment comprising:
a plurality of connected crowns along an edge of said first segment comprising a first connected crown along an edge of said first segment;
a plurality of unconnected crowns along said edge of said first segment comprising:
a first unconnected neighbor crown directly adjacent but spaced apart from said first connected crown; and
a second unconnected neighbor crown directly adjacent but spaced apart from said first connected crown;
wherein two and only two of said plurality of unconnected crowns along said edge of said first segment are between each connected crown along said edge of said first segment, said connected crowns being connected to tabs;
a first tab of said tabs comprising:
a first tab end; and
a second tab end, wherein said first connected crown is connected to approximately a middle of said first tab between said first tab end and said second tab end, said method comprising:
moving said first and second unconnected neighbor crowns closer to said first connected crown; and
moving said middle of said first tab and said first connected crown radially inwards with respect to said first and second unconnected neighbor crowns by applying an inward force to only said first tab end and said second tab end, wherein said first and second unconnected neighbor crowns overlap said first connected crown, wherein said first tab contacts said sheath only at said first tab end and said second tab end of said first tab.

5. A method of loading a stent into a sheath, wherein prior to said loading, said stent comprises:
a first segment comprising:
a plurality of connected crowns along an edge of said first segment comprising a first connected crown along an edge of said first segment;
a plurality of unconnected crowns along said edge of said first segment comprising:
a first unconnected neighbor crown directly adjacent but spaced apart from said first connected crown; and
a second unconnected neighbor crown directly adjacent but spaced apart from said first connected crown;
wherein two and only two of said plurality of unconnected crowns along said edge of said first segment are between each connected crown along said edge of said first segment, said connected crowns being connected to tabs;
a first tab of said tabs comprising:
a first tab end; and
a second tab end, wherein said first connected crown is connected to approximately a middle of said first tab between said first tab end and said second tab end, said method comprising:
moving said first and second unconnected neighbor crowns closer to said first connected crown; and
moving said middle of said first tab and said first connected crown radially inwards with respect to said first and second unconnected neighbor crowns by applying an inward force to only said first tab end and said second tab end, wherein said first and second unconnected neighbor crowns overlap said first connected crown, wherein said middle of said first tab is spaced apart from said sheath.

6. A method of loading a stent into a sheath, wherein prior to said loading, said stent comprises:
a first segment comprising:
a plurality of connected crowns along an edge of said first segment comprising a first connected crown along an edge of said first segment;
a plurality of unconnected crowns along said edge of said first segment comprising:
a first unconnected neighbor crown directly adjacent but spaced apart from said first connected crown; and
a second unconnected neighbor crown directly adjacent but spaced apart from said first connected crown;

wherein two and only two of said plurality of unconnected crowns along said edge of said first segment are between each connected crown along said edge of said first segment, said connected crowns being connected to tabs;
a first tab of said tabs comprising:
 a first tab end; and
 a second tab end, wherein said first connected crown is connected to approximately a middle of said first tab between said first tab end and said second tab end, said method comprising:
moving said first and second unconnected neighbor crowns closer to said first connected crown; and
moving said middle of said first tab and said first connected crown radially inwards with respect to said first and second unconnected neighbor crowns by applying an inward force to only said first tab end and said second tab end, wherein said first and second unconnected neighbor crowns overlap said first connected crown, wherein said tabs have a first radius of curvature before said loading, said tabs retaining said first radius of curvature during said loading.

7. A method of loading a stent into a sheath, wherein prior to said loading, said stent comprises:
 a first segment comprising:
  a plurality of connected crowns along an edge of said first segment comprising a first connected crown along an edge of said first segment;
  a plurality of unconnected crowns along said edge of said first segment comprising:
   a first unconnected neighbor crown directly adjacent but spaced apart from said first connected crown; and
   a second unconnected neighbor crown directly adjacent but spaced apart from said first connected crown;
   wherein two and only two of said plurality of unconnected crowns along said edge of said first segment are between each connected crown along said edge of said first segment, said connected crowns being connected to tabs;
a first tab of said tabs comprising:
 a first tab end; and
 a second tab end, wherein said first connected crown is connected to approximately a middle of said first tab between said first tab end and said second tab end, said method comprising:
moving said first and second unconnected neighbor crowns closer to said first connected crown; and
moving said middle of said first tab and said first connected crown radially inwards with respect to said first and second unconnected neighbor crowns by applying an inward force to only said first tab end and said second tab end, wherein said first and second unconnected neighbor crowns overlap said first connected crown, wherein said first tab retains a curvature radius greater than the sheath during said loading.

\* \* \* \* \*